United States Patent
Schumacher

(10) Patent No.: US 6,752,808 B2
(45) Date of Patent: Jun. 22, 2004

(54) BONE DISTRACTOR WITH SHAFT EXTENSION

(75) Inventor: Brian Schumacher, Jacksonville, FL (US)

(73) Assignee: Walter Lorenz Surgical, Inc., Jacksonville, FL (US)

(*) Notice: Subject to any disclaimer, the term of this patent is extended or adjusted under 35 U.S.C. 154(b) by 211 days.

(21) Appl. No.: 09/998,272

(22) Filed: Nov. 30, 2001

(65) Prior Publication Data

US 2002/0035368 A1 Mar. 21, 2002

Related U.S. Application Data

(63) Continuation of application No. 09/394,609, filed on Sep. 13, 1999, now Pat. No. 6,383,189.

(51) Int. Cl.[7] ............................................. A61B 17/58
(52) U.S. Cl. ......................................................... 606/90
(58) Field of Search ............................. 606/57, 58, 90, 606/105, 59, 86

(56) References Cited

U.S. PATENT DOCUMENTS

| 4,730,608 A | * | 3/1988 | Schlein .......................... 606/57 |
| 4,848,368 A | * | 7/1989 | Kronner ........................ 606/57 |
| 5,769,850 A | * | 6/1998 | Chin ............................ 606/53 |
| 5,902,304 A | * | 5/1999 | Walker et al. ................. 606/71 |

* cited by examiner

*Primary Examiner*—Eduardo C. Robert
(74) *Attorney, Agent, or Firm*—Harness, Dickey & Pierce, P.L.C.

(57) ABSTRACT

A bone distractor for distracting bone on opposite sides of an osteotomy of the bone includes a first affixation member for affixation to the bone on one side of the osteotomy and a second affixation member for affixation to the bone on another side of the osteotomy. A rotatable member engages the first and second affixation members to distract the first and second affixation members relative to each other in response to rotation of the rotatable member. An extension member is removably connectable to the rotatable member for imparting torque thereto when rotated. The extension member can be flexible to permit elastic bending while imparting torque.

3 Claims, 2 Drawing Sheets

BONE DISTRACTOR WITH SHAFT EXTENSION

CROSS-REFERENCE TO RELATED APPLICATIONS

This application is a continuation of U.S. patent application Ser. No. 09/394,609 filed on Sep. 13, 1999, now U.S. Pat. No. 6,383,189, which is incorporated herein by reference.

FIELD OF THE INVENTION

The present invention relates generally to apparatus for correction of craniofacial abnormalities, and more particularly to apparatus for affixation to maxillary or mandibular bones to effect distraction of the bones relative to a fracture or osteotomy.

BACKGROUND OF THE INVENTION

Various developmental disorders of the human skull result in craniofacial abnormalities in which certain bones fail to grow in proper proportion to other bones, or in which certain bones fuse prematurely, causing malformation of the midface or mandible. It is known to correct such abnormalities by separating the bones through osteotomy or fracture, and then slowly distracting the bones relative to each other, thereby inducing bone growth at the separation line. As the bones are distracted, the newly formed bone at the growth surfaces adjacent the separation fills in the increasing gap between the bones. By this method, the midface of the cranium can be advanced forward, or the mandible can be lengthened, for example.

Apparatus for effecting distraction can involve two affixation members, in which each affixation member is temporarily affixed to the bone on opposite sides of the osteotomy, such as by bone screws, and a screw drive member that threadedly engages at least one of the affixation members. By rotating the screw drive member incrementally and periodically, the two affixation members are driven apart, and hence the bones on either side of the osteotomy are distracted relative to the location of the osteotomy. Typically, after the desired amount of distraction is achieved and the new bone growth is sufficiently consolidated, the distraction apparatus is removed.

While the distraction apparatus is in place, the screw drive member must be accessed periodically, typically via the oral cavity, so that a driver can be engaged with the screw drive member to apply torque thereto. Often the location and orientation of the distraction apparatus are such that access to the driven end of the screw drive member is difficult or awkward. To address this problem, universal joints have been used to permit alignment of the driving end of the driver with the driven end of the screw drive member of the distraction apparatus, while permitting the handle of the driver to be oriented at a convenient angle, often outside the oral cavity. Such universal joints can be bulky and do not always provide the desired degree of angular adjustment between the handle of the driver and the driving end of the driver.

It would be advantageous to provide an improved distractor apparatus having a driven member that is more easily accessed by an external driver through the oral cavity. The present invention, an embodiment of which is described below with reference to the drawings, provides this and other advantages.

SUMMARY OF THE INVENTION

In accordance with one aspect of the present invention, a bone distractor is provided for distracting bone on opposite sides of an osteotomy of the bone. The bone distractor includes a first affixation member for affixation to the bone on one side of the osteotomy, and a second affixation member for affixation to the bone on another side of the osteotomy. A screw means has a rotatable member that engages the first and second affixation members for distracting the first and second affixation members relative to each other in response to rotation of the rotatable member. An extension has means for removably connecting the extension to the rotatable member of the screw means and for imparting torque to the rotatable member when connected thereto and the extension is rotated.

According to another aspect of the present invention, the extension includes a flexible shaft capable of bending elastically while imparting torque.

It is an object of the present invention to provide an improved bone distractor that is readily accessible for incremental distraction while emplaced in a patient.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
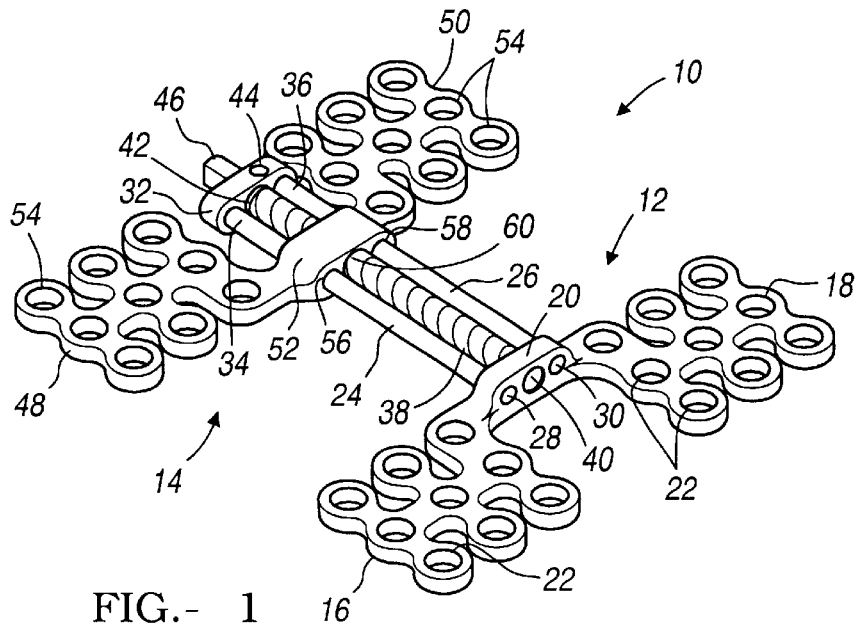
FIG. 1 is a perspective view of a bone distractor in accordance with the present invention.
Figure 2:
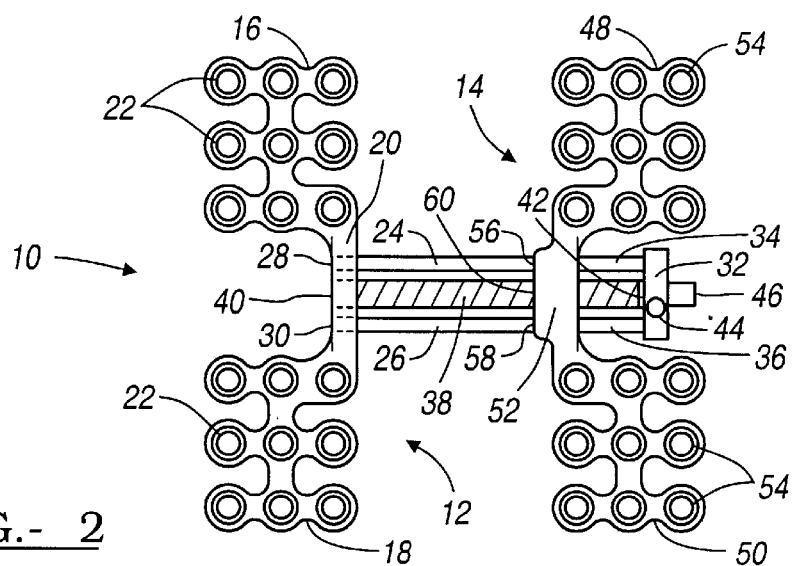
FIG. 2 is a plan view of the bone distractor of FIG. 1.
Figure 3:
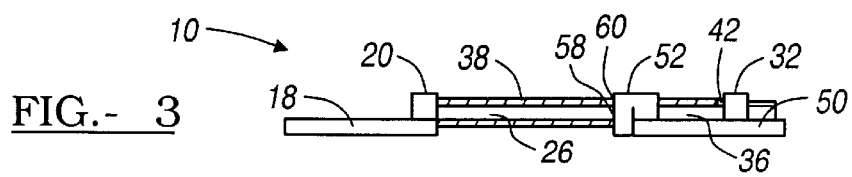
FIG. 3 is a side view of the bone distractor of FIG. 2.

Referring to FIGS. 1, 2 and 3, a preferred embodiment of a bone distractor apparatus 10, constructed in accordance with the present invention, is illustrated. Bone distractor apparatus 10 includes a first affixation member 12, and a second affixation member 14 that is moveable relative to first affixation member 12. A pair of wing elements 16 and 18 extend transversely from a central bridge portion 20 of first affixation member 12. Each wing element 16 and 18 is substantially planar and includes a plurality of screw holes 22 for receiving bone screws therethrough to secure wing elements 16 and 18 to bone, with wing elements 16 and 18 lying flat adjacent to the bone surface. Extending longitudinally, generally parallel to the plane in which wing elements 16 and 18 lie, are a pair of parallel rods 24 and 26. First ends 28 and 30 of rods 24 and 26, respectively, are friction fitted within corresponding holes in bridge portion 20 of first affixation member 12. An end member 32 has holes spaced the same as the rod holes in bridge element 20 for receiving second ends 34 and 36 of rods 24 and 26 in similar friction fit. A threaded screw rod 38 has a first non-threaded end 40 received for free rotation within a corresponding hole in bridge member 20 located between the holes in which rods 24 and 26 are received. Screw rod 38 has a second non-threaded portion 42 received for free rotation within a corresponding hole in end member 32 located between the holes in which rods 24 and 26 are received. Non-threaded portion 42 includes an annular groove disposed within the corresponding hole in end member 32. A pin 44 received through a cross-bore in end member 32 lies perpendicular to screw rod 38 and engages the annular groove in non-threaded portion 42 to restrain screw rod 38 against axial movement relative to end member 32, and hence (via rods 24 and 26) against axial movement relative to bridge member 20 of first affixation member 12. A driven end 46 of screw rod 38 extends outwardly beyond end member 32. Driven end 46 has a square cross-section for engaging a driving tool. A pair of wing elements 48 and 50 extend transversely from a central bridge portion 52 of second affixation member 14. Each wing element 48 and 50 is substantially planar and includes a plurality of screw holes 54 for receiving bone screws therethrough to secure wing elements 48 and 50 to bone, with wing elements 48 and 50 lying flat adjacent to the bone surface. Holes 56 and 58, spaced to receive rods 24 and 26 therethrough, extend longitudinally through bridge portion 52 and are sized for a free sliding relationship between second affixation member 14 and rods 24 and 26. A threaded hole 60 extends longitudinally through bridge portion 52 between holes 56 and 58, and screw rod 38 is threadedly received in threaded hole 60.

In use, distraction apparatus 10 is emplaced with wing members 16 and 18 of first affixation member 12 on one side of an osteotomy of the mandible, for example, and wing members 48 and 50 of second affixation member 14 on the other side of the osteotomy. Each of wing members 16, 18, 48 and 50 are bent as necessary to lie flat adjacent the bone, and bone screws are inserted through screw holes 22 and 54 to secure first and second affixation members 12 and 14 to respective bones on each side of the osteotomy. Distraction is effected by engaging square driven end 46 of screw rod 38 with a suitable driver tool. Torque applied to screw rod 38 causes screw rod 38 to turn, rotating freely relative to first affixation member 12 and with respect to end member 32, but in threaded engagement with second affixation member 14. Consequently, second affixation member 14 is caused to move longitudinally relative to first affixation member 12, sliding on rods 24 and 26. By rotating screw rod 38 in the appropriate direction, the respective bones to which first and second affixation members 12 and 14 are affixed are distracted relative to one another. The amount of distraction per rotation of screw rod 38 is determined by the pitch of the thread.

Figure 4:
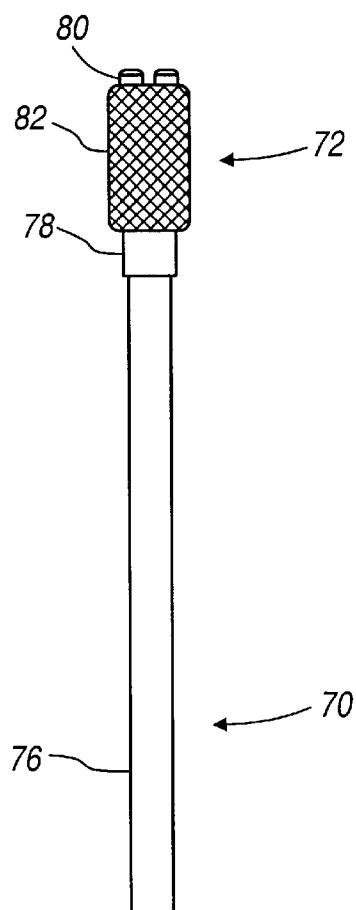
FIG. 4 is a side view of a flexible extension useful in combination with the bone distractor of FIG. 1.

Referring to FIG. 4, a flexible extension 70 is illustrated. Flexible extension 70 includes a driver connector 72 at one end, a driven connector 74 at the other end, and a flexible shaft portion 76 therebetween. Driving connector 72 includes a body 78 crimped onto one end of flexible shaft portion 76 for rotation therewith. Extending longitudinally from body 78 is a split barrel 80 having a recess therein open to the end of barrel 80 and having a square internal cross-section sized to receive in driving engagement driven end 46 of screw rod 38 of distractor apparatus 10. Split barrel 80 is externally threaded. An externally knurled sleeve 82, internally threaded, is received in threaded engagement on barrel 80. Split barrel 80 includes a non-threaded exterior portion adjacent the free end thereof that tapers to a larger diameter toward the free end. As sleeve 82 is rotated relative to split barrel 80, such that sleeve 82 is displaced toward the free end of barrel 80, sleeve 82 engages the tapered free end of split barrel 80 and urges split barrel 80 to contract diametrically. Driven connector 74 includes a body 84 crimped onto the other end of flexible shaft portion 76 for rotation therewith. Extending longitudinally from body 78 is a square cross-section driven portion 86, sized similarly to driven end 46 of screw rod 38 of distractor apparatus 10. Flexible shaft portion 76 comprises a closely wound wire spiral, preferably stainless steel, configured for elastic bending and flexing, yet capable of transmitting torque without undue torsional displacement. Alternatively, shaft portion 76 can be a non-flexing rod for use in applications in which an extension is desired, but angular realignment is not needed.

In use, flexible extension 70 is attached to distraction apparatus 10 by connecting driving connector 72 to driven end 46 of screw rod 38 such that driven end 46 is received in driving engagement within split barrel 80. Sleeve 82 is turned and threadedly advanced toward the free end of barrel 80, such that barrel 80 contracts diametrically and clamps onto driven end 46, thereby securing flexible extension 70 to distraction apparatus 10 against relative axial movement or disengagement. A suitable driving tool can be engaged with driven portion 86 and rotated, whereby torque is transmitted via flexible extension 70 to screw rod 38 of distraction apparatus 10 of FIG. 1. Flexible extension 70 is of such length as permits ready and convenient access to driven end 86 for the duration of the two to four week period during which distraction apparatus 10 is advanced. After distraction is completed, flexible extension 70 can be removed from distraction apparatus 10 to enhance the comfort of the patient for the duration of the one to three month period of bone consolidation that follows. As preferred, the length of flexible extension 70 is such that it is wholly contained within the oral cavity. Alternatively, for some applications, flexible extension 70 can extend outside the oral cavity through an incision in the cheek, for example.

Figure 5:
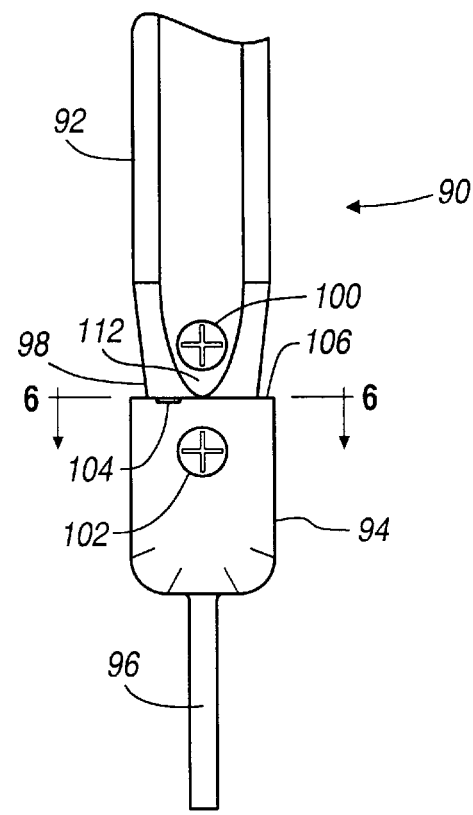
FIG. 5 is a side view of a driver tool useful in combination with the bone distractor of FIG. 1 and/or the flexible extension of FIG. 4.
Figure 6:
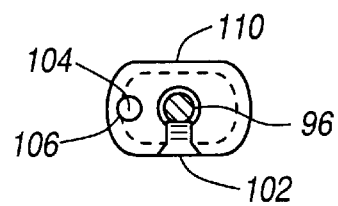
FIG. 6 is a cross-sectional view of the driver tool of FIG. 5, taken in plane 6—6 and viewed in the direction of the arrows.

Referring to FIGS. 5 and 6, a driver tool 90 is illustrated. Driver tool 90 is useful for engaging and transmitting torque to the flexible extension 70 and/or screw rod 38 of distraction apparatus 10. Driver tool 90 is also useful for determining the number of rotations imparted to flexible extension 70 and/or screw rod 38, by emitting an audible click for each 180 degrees of rotation. Driver tool 90 includes a main handle 92, an auxiliary handle 94, and a drive blade 96. Main handle 92 is affixed to drive blade 96 for rotation therewith, whereas auxiliary handle 94 is arranged for rotation about drive blade 96 relative to main handle 92. Drive blade 96, having a round exterior cross-section, is received in a longitudinal bore in distal end 98 of main handle 92. A screw 100 is received in a threaded transverse bore that intersects the bore in which drive blade 96 is received in main handle 92. Screw 100 engages drive blade 96 to secure drive blade 96 to main handle 92 against relative rotation and axial displacement. Auxiliary handle 94 includes a longitudinal bore therethrough sized to permit drive blade 96 to be received therein for relative rotation between auxiliary handle 94 and drive blade 96. A screw 102 is received in a threaded transverse bore that intersects the bore in which drive blade 96 is received in auxiliary handle 94. Screw 102 extends within an annular groove in drive blade 96 to prevent axial displacement of auxiliary handle 94 relative to drive blade 96, while permitting rotation of auxiliary handle 94 relative to drive blade 96. A bore in end face 106 of auxiliary handle 94 contains a spring biased ball detent 104 in which a ball is biased outwardly from end face 106, yet retained against escaping. The ball detent 104 bears against end face 108 of main handle 92 when the flats 110 and 112 of auxiliary handle 94 and main handle 92 are aligned. As main handle 92 is rotated relative to auxiliary handle 94, flat 112 moves past alignment with ball detent 104 and the ball snaps outward, free of engagement with the end face 108 of main handle 92. Such movement of ball detent 104 results in an audible click. Another 180 degrees of rotation results in ball detent first becoming depressed by engagement with end face 108 of main handle 92, and then snapping free again as the flat on the other side of main handle 92 aligns with ball detent 104. Thus, for each full rotation of auxiliary handle 94 relative to main handle 92, two audible clicks are generated. A recess in the free end of drive blade 96 has a square internal cross-section sized to engage driven end 86 of flexible extension 70 or driven end 46 of drive screw 38 of distraction apparatus 10.

In use, the recess in the free end of blade 96 is engaged with driven end 86 of flexible extension 70 or driven end 46 of drive screw 38 of distraction apparatus 10. While holding the flats 110 of auxiliary handle 94 with the thumb and fingers of one hand to prevent auxiliary handle 94 from rotating, the main handle 92 is rotated, causing drive blade 96 to rotate and impart torque to flexible extension 70 or drive screw 38. With each 180 degrees of rotation of main handle 92 relative to auxiliary handle 94, an audible click is generated. Multiplying the number of clicks heard by one-half the thread pitch of screw rod 38 gives the amount by which second affixation member 14 is distracted from first affixation member 12.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A bone distractor for distracting bone on opposite sides of an osteotomy of said bone, comprising;

a first affixation member for affixation to said bone on one side of said osteotomy;

a second affixation member for affixation to said bone on another side of said osteotomy;

a rotatable member engaging said first affixation member and said second affixation member for distracting said first and second affixation members relative to each other in response to rotation of said rotatable member; and an extension removably connected to said rotatable member at a connection and having a flexible shaft bendable at more than one location along its length, said connection imparting torque to said rotatable member when connected thereto and said extension is rotated.

2. The bone distractor of claim 1, wherein said connection includes a sleeve axially moveable along a clamping body.

3. The bone distractor of claim 1, wherein said flexible shaft is elastically bendable.

* * * * *

UNITED STATES PATENT AND TRADEMARK OFFICE
CERTIFICATE OF CORRECTION

PATENT NO. : 6,752,808 B2  
DATED : June 22, 2004  
INVENTOR(S) : Brian Schumacher It is certified that error appears in the above-identified patent and that said Letters Patent is hereby corrected as shown below:

Title page,
Item [56], References Cited, U.S. PATENT DOCUMENTS, insert the following:
```
-- 4,187,841   02/12/1980   Knutson
   5,314,426   05/24/1994   Pohl et al.
   5,364,396   11/15/1994   Robinson et. al.
   5,807,382   09/15/1998   Chin
   5,855,580   01/05/1999   Kreidler et al.
   5,899,902   05/04/1999   Middleton
   6,093,189   07/25/2000   Sellers --.
```

Column 6,
Line 10, "comprisign;" should be -- comprising: --.

Signed and Sealed this

Third Day of May, 2005

JON W. DUDAS  
*Director of the United States Patent and Trademark Office*